United States Patent
Bak et al.

(10) Patent No.: US 11,178,833 B1
(45) Date of Patent: Nov. 23, 2021

(54) *MONOLENA* PLANT 'MIDNIGHT GLORY'

(71) Applicant: Corn Bak BV, Assendelft (NL)

(72) Inventors: Elly Bak, Rijsenhout (NL); Nicolaas D. M. Steur, Oude Niedorp (NL)

(73) Assignee: Corn Bak B.V.

( * ) Notice: Subject to any disclaimer, the term of this patent is extended or adjusted under 35 U.S.C. 154(b) by 0 days.

(21) Appl. No.: 16/869,231

(22) Filed: May 7, 2020

(51) Int. Cl.
*A01H 5/10* (2018.01)
*A01H 6/00* (2018.01)

(52) U.S. Cl.
CPC ............... *A01H 5/10* (2013.01); *A01H 6/00* (2018.05)

(58) Field of Classification Search
None
See application file for complete search history.

*Primary Examiner* — Medina A Ibrahim
(74) *Attorney, Agent, or Firm* — Cassandra Bright

(57) ABSTRACT

A new and distinct Monolena cultivar named 'MIDNIGHT GLORY' characterized by its medium plant size and year round growth. Plants have long-lasting qualities as an indoor ornamental plant. Foliage is decorative and uniquely colored greyed-purple and dark yellow-green.

5 Claims, 1 Drawing Sheet
(1 of 1 Drawing Sheet(s) Filed in Color)

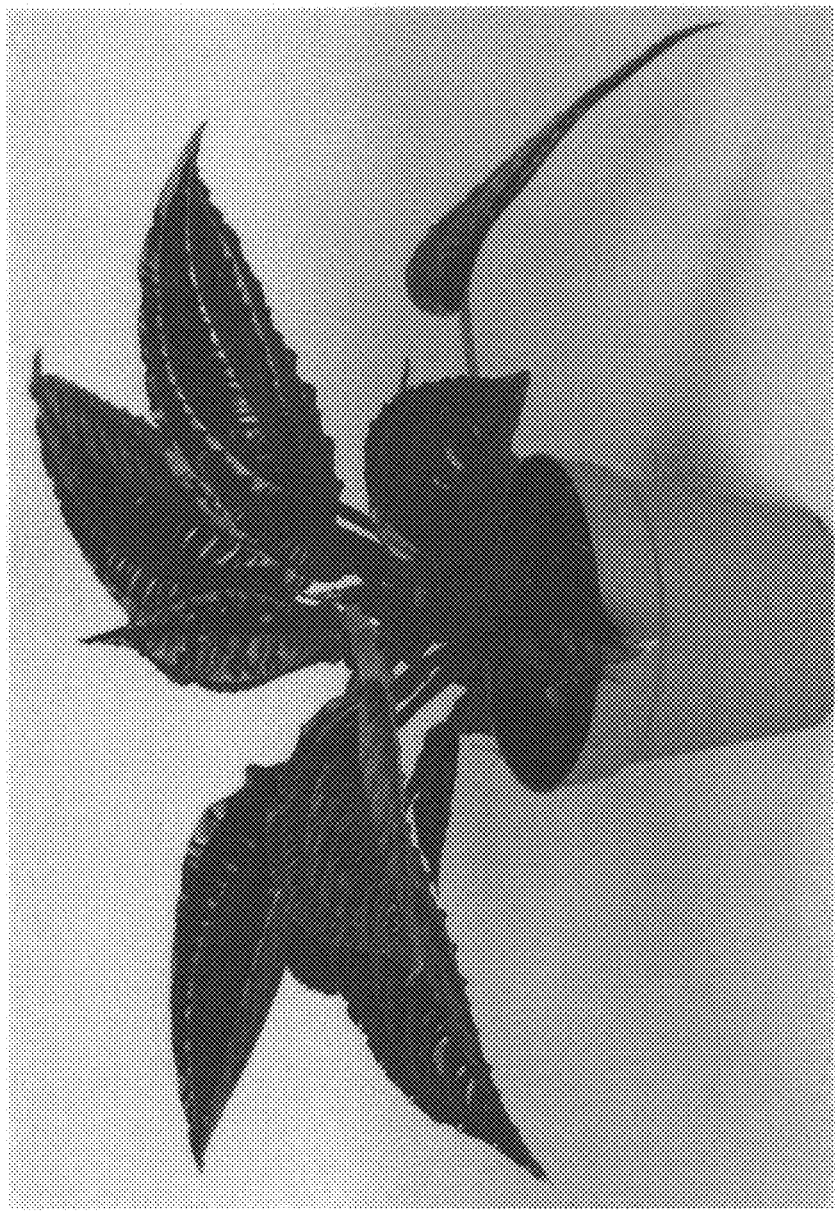

MONOLENA PLANT 'MIDNIGHT GLORY'

FIELD OF THE INVENTION

The present invention relates to a new, distinct and stable cultivar of Monolena, hereinafter referred to as 'MIDNIGHT GLORY'. The present invention relates to seeds which are the Monolena 'MIDNIGHT GLORY', as well as, plants and plant parts produced by these seeds which have all of the morphological and physiological characteristics of the Monolena cultivar 'MIDNIGHT GLORY'. The present invention also relates to methods for producing these seeds and plants of the Monolena cultivar 'MIDNIGHT GLORY'. Furthermore, the present invention relates to a method of producing progeny Monolena plants by crossing Monolena 'MIDNIGHT GLORY', as either the female or seed or male or pollen parent, with another Monolena plant and selecting progeny.

BACKGROUND OF THE INVENTION

The present invention relates to a new, distinct and stable cultivar, botanically known as Monolena primultflora, and hereinafter referred to by the variety denomination 'MIDNIGHT GLORY'. The new Monolena 'MIDNIGHT GLORY' originated from a familial cross of unnamed proprietary seedlings. Development of the parent varieties was conducted over several years, as part of a controlled breeding program by the inventors. The cross resulting in the new variety 'MIDNIGHT GLORY' was made during 2018. 'MIDNIGHT GLORY' first flowered in 2019, in Assendelft, The Netherlands. The objective of the breeding program is to create new Monolena plants with interesting characteristics for the ornamental market. Characteristics sought included durable plants with long-lastingness for indoor ornamental uses, as well as colorful foliage.

Monolena is a member of the Melastomataceae family. Monolena primultflora is native to Peru and Ecuador. In its native moist habitat plants grow epiphytically. Plants under cultivation are terrestrial. Plants consist of a basal caudex, from which emerges a rosette of decorative foliage. Flowers are not considered to have ornamental value.

Monolena primultflora are not well-known in the industry at this time. Some specialty growers of novelty ornamental plants offer unnamed selections of Monolena primultflora in small quantities. The new cultivar with its unique greyed-purple and dark yellow-green foliage coloration and phenotypically uniform reproduction from seed is a novel and useful introduction to the ornamental plant market. Monolena cultivars that can be easily propagated by seed, and reproduce the desired features consistently are a valuable introduction to the horticultural industry.

The new Monolena 'MIDNIGHT GLORY' was developed through a controlled breeding program and exhibits unique, desirable and stable characteristics.

SUMMARY OF THE INVENTION

The present invention provides Monolena plant selections that are a long-lasting medium sized, cultivar having greyed-purple and dark yellow-green foliage.

These and other objectives have been achieved in accordance with the present invention which provides 'MIDNIGHT GLORY' as a new Monolena cultivar that is a product of a planned breeding program conducted by the inventors, Elly Bak and Nico D. M. Steur, in Assendelft, The Netherlands. The cross resulting in the new cultivar 'MIDNIGHT GLORY' is a familial cross of proprietary seedlings which have a sufficient degree of homozygosity such that the progeny of the cross are genotypically and phenotypically uniform. The new cultivar 'MIDNIGHT GLORY' therefore can be produced by sexual reproduction by crossing the parental to produce a population of progeny plants, each of which has the combination of characteristics as herein disclosed for the new variety 'MIDNIGHT GLORY'.

Seeds which are the cultivar 'MIDNIGHT GLORY' are produced by crossing the parental selections and have been deposited with the NCIMB limited, Ferguson Building, Craibstone Estate, Bucksburn, Aberdeen, AB21 9YA, United Kingdom.

OBJECTS OF THE INVENTION

The present invention relates to seeds which produce Monolena 'MIDNIGHT GLORY'. The present invention also relates to Monolena plants, and parts thereof, having all the physiological and morphological characteristics of Monolena 'MIDNIGHT GLORY'. The present invention relates to a plant produced from seeds which are Monolena 'MIDNIGHT GLORY'. The present invention also relates to plant parts, such as pollen, seeds or inflorescence produced by Monolena 'MIDNIGHT GLORY'.

The present invention relates to a method of producing seed which are Monolena 'MIDNIGHT GLORY', by a crossing the unpatented proprietary parent selections of Monolena primuliflora and harvesting seeds produced from said cross.

The present invention also relates to a method of producing plants having all the physiological and morphological characteristics of the Monolena 'MIDNIGHT GLORY' comprising the steps of (a) crossing the proprietary parent selections of Monolena primuliflora (unpatented). (b) harvesting seeds produced from said cross; and (c) producing plants from said harvested seeds.

BRIEF DESCRIPTION OF THE INVENTION

The following traits have been repeatedly observed and are determined to be unique characteristics of 'MIDNIGHT GLORY' which in combination distinguish this Monolena as a new and distinct cultivar:
1. Year-round growth.
2. Ornamental foliage plant with decorative greyed-purple and dark yellow-green foliage.
3. Long-lasting qualities as an indoor ornamental plant.
4. Medium sized plant.

The new Monolena 'MIDNIGHT GLORY' can be compared to the unpatented unnamed Monolena primuliflora sold in specialty nurseries. Plants of the new cultivar 'MIDNIGHT GLORY' are similar to plants of these Monolena primuliflora plants in most horticultural characteristics, however the varieties differ in the following:
1. Monolena 'Midnight Glory' produces foliage with distinctive under surface coloration of greyed-purple, and a dark yellow-green upper surface, this comparator has light green foliage.
2. Plants of this comparator are less vigorous.
3. Plants of this comparator are not produced uniformly from seed.

'MIDNIGHT GLORY' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

BRIEF DESCRIPTION OF THE PHOTOGRAPH

The patent or application file contains at least one drawing executed in color. Copies of this patent or patent application publication with color drawings will be provided by the Office upon request and payment of the necessary fees.

The accompanying photograph illustrates the overall appearance of the new Monolena cultivar 'MIDNIGHT GLORY' showing the colors as true as is reasonably possible with colored reproductions of this type. Colors in the photograph may differ slightly from the color values cited in the detailed botanical description which accurately describes the color of 'MIDNIGHT GLORY'.

The accompanying drawing shows a side view perspective of a typical potted plant of 'MIDNIGHT GLORY', at approximately 6 months of age from potting size in a 13 cm pot.

DETAILED BOTANICAL DESCRIPTION

The present invention was created by the inventors, Elly Bak and Nicolaas D. M. Steur in 2018 and flowered for the first time in 2019 in Assendelft, The Netherlands.

This invention is directed to Monolena plant having all the morphological and physiological characteristics of the cultivar 'MIDNIGHT GLORY' produced from seeds which are the product of the cross of the proprietary parental selections of Monolena primuliflora Both parents have a sufficient degree of homozygosity such that the progeny of the cross were, and continue to be, phenotypically uniform. The new cultivar 'MIDNIGHT GLORY' can therefore be produced by sexual reproduction by crossing of the parental Monolena primuliflora selections to produce a population of progeny plants, each of which has the combination of characteristics herein disclosed for the new cultivar 'MIDNIGHT GLORY'.

The new cultivar 'MIDNIGHT GLORY' has not been produced asexually, however this is likely possible, though not commercially viable. asexually reproducing progeny from the cross of the parental selections. Sexually reproduced progeny have demonstrated that the new cultivar reproduces true-to-type and that the combination of characteristics as herein disclosed for the new cultivar are firmly fixed and predictable.

The aforementioned photograph, together with the following observations, measurements and values describe the new Monolena primuliflora 'MIDNIGHT GLORY' as grown in a greenhouse in Assendelft, The Netherlands, under conditions which closely approximate those generally used in commercial practice. Plants of 'MIDNIGHT GLORY' were grown in a greenhouse with day temperatures ranging from 20° C. to 28° C. and night temperatures ranging from 18° C. to 23° C. No artificial lighting or photoperiodic treatments were conducted.

Color references are made to the Royal Horticultural Society Color Chart (RHS), 2015 edition, except where general colors of ordinary significance are used. Color values were taken under daylight conditions in a greenhouse in Assendelft, The Netherlands.

CLASSIFICATION

Botanical: Monolena primuliflora.

PLANT

General Appearance and Form: Tender herbaceous plant composed of a basal caudex and rosette forming foliage.
Height: Approx. 22 cm
Width: About 55 cm
Shape: Rosette
Growth habit: Upright outwardly arching growth habit. Rosette leaves are erect when young, becoming outwardly arching with development.
Plant Vigor: Good
Caudex: About 4 cm in a 13 cm pot, colored near RHS Yellow-Green 144B, smooth texture.
Cold Tolerance: Frost tender. Temperatures below 5° C. may damage plants.

FOLIAGE

Arrangement: Rosette
Size of leaf:
length: Average 21 cm
width: Average 13 cm
Shape of leaf: Ovate
Apex: Acuminate
Margin: Ciliate
Color:
Immature:
Upperside: Near RHS Yellow-Green 146A, base flushed Red-Purple
59B, mid-section flushed Greyed-Purple 187B.
Underside: Near RHS Red-Purple 59B
Mature:
Upperside: Near RHS Yellow-Green 147A
Underside: Near RHS Greyed-Purple 187A
Quantity: Average 14, in a 13 cm pot.
Petiole:
Length: Average 12 cm
Width: Average 0.6 cm
Color: Near RHS Greyed-Purple 187A
Texture: Smooth

INFLORESCENCE

Type: Raceme
Quantity: About 6 per plant
Flower Quantity per Inflorescence: 2 to 8
Length of flowering stem: approx. 20 cm
Color: Near RHS Greyed-Purple 187A.
Individual flowers;
Length: 3.2 cm
Diameter: 1.0 cm
Petal quantity: 5
Petal length: 1.4 cm
Petal width: 0.8 cm
Petal color: Near RHS White 155 D flushed Purple 78D, upper and lower surfaces.

REPRODUCTIVE ORGANS

Stamen:
Quantity: 10 per flower
Length: Approximately 1.1 cm
Style: Approximately 1 cm
SEEDS/FRUIT: Grit like seed produced in capsules.
DISEASE/PEST RESISTANCE: Not observed to date.
DISEASE/PEST SUSCEPTIBILITY: Not observed to date.

We claim:

1. A *Monolena* plant named 'MIDNIGHT GLORY', representative seed deposited at the NCIMB in Aberdeen, Scotland, NCIMB having accession number 43618.

2. A *Monolena* seed that produces the plant of claim 1.

3. A plant part obtained from the *Monolena* plant of claim 1.

4. A method of producing *Monolena* progeny plant comprising the steps of
   (a) crossing *Monolena* 'MIDNIGHT GLORY', representative seed of said plant having been deposited at the NCIMB, having accession number NCIMB 43618, as a female or male parent with another *Monolena* plant, and
   (b) selecting progeny.

5. The method according to claim 4, wherein the second *Monolena* plant is 'MIDNIGHT GLORY', representative seed of said plant having been deposited at the NCIMB, assigned accession number 43618.

* * * * *